United States Patent [19]
Sunnen

[11] Patent Number: 6,073,627
[45] Date of Patent: Jun. 13, 2000

[54] APPARATUS FOR THE APPLICATION OF OZONE/OXYGEN FOR THE TREATMENT OF EXTERNAL PATHOGENIC CONDITIONS

[75] Inventor: Gerard V. Sunnen, New York, N.Y.

[73] Assignee: Medizone International, Inc., Stinson Beach, Calif.

[21] Appl. No.: 09/126,504

[22] Filed: Jul. 30, 1998

[51] Int. Cl.[7] ................................................ A61M 15/02
[52] U.S. Cl. ................................ 128/202.25; 128/203.16
[58] Field of Search ........................ 128/202.25, 203.16, 128/205.26; 601/41, 43, 44

[56] References Cited

U.S. PATENT DOCUMENTS

| | | | |
|---|---|---|---|
| 1,773,220 | 8/1930 | Credicott | 128/202.25 |
| 2,920,622 | 1/1960 | Steel | 128/202.25 |
| 3,096,762 | 7/1963 | Winchell | 128/202.25 |
| 4,375,812 | 3/1983 | Vaseen et al. | 128/202.25 |
| 5,052,382 | 10/1991 | Wainwright | 128/202.25 |
| 5,179,943 | 1/1993 | Hama et al. | 128/202.25 |
| 5,188,099 | 2/1993 | Todeschini et al. | 128/205.26 |
| 5,359,997 | 11/1994 | Rigo et al. | 128/202.25 |
| 5,381,789 | 1/1995 | Marquardt | 128/202.25 |

*Primary Examiner*—Aaron J. Lewis
*Attorney, Agent, or Firm*—Morgan & Finnegan, L.L.P.

[57] ABSTRACT

There is disclosed a delivery system for providing ozone to a patient having an external pathogenic condition. The system has an ozone generation portion and a delivery portion which includes a source of oxygen connected to an ozone generator and a delivery portion which is a flexible envelope for encompassing a portion of a patient to be treated. The system also includes cooperative elements and gauges to provide and precisely control the amounts of ozone and physical properties thereof very precisely in order to provide the desired treatment to the patient.

9 Claims, 1 Drawing Sheet

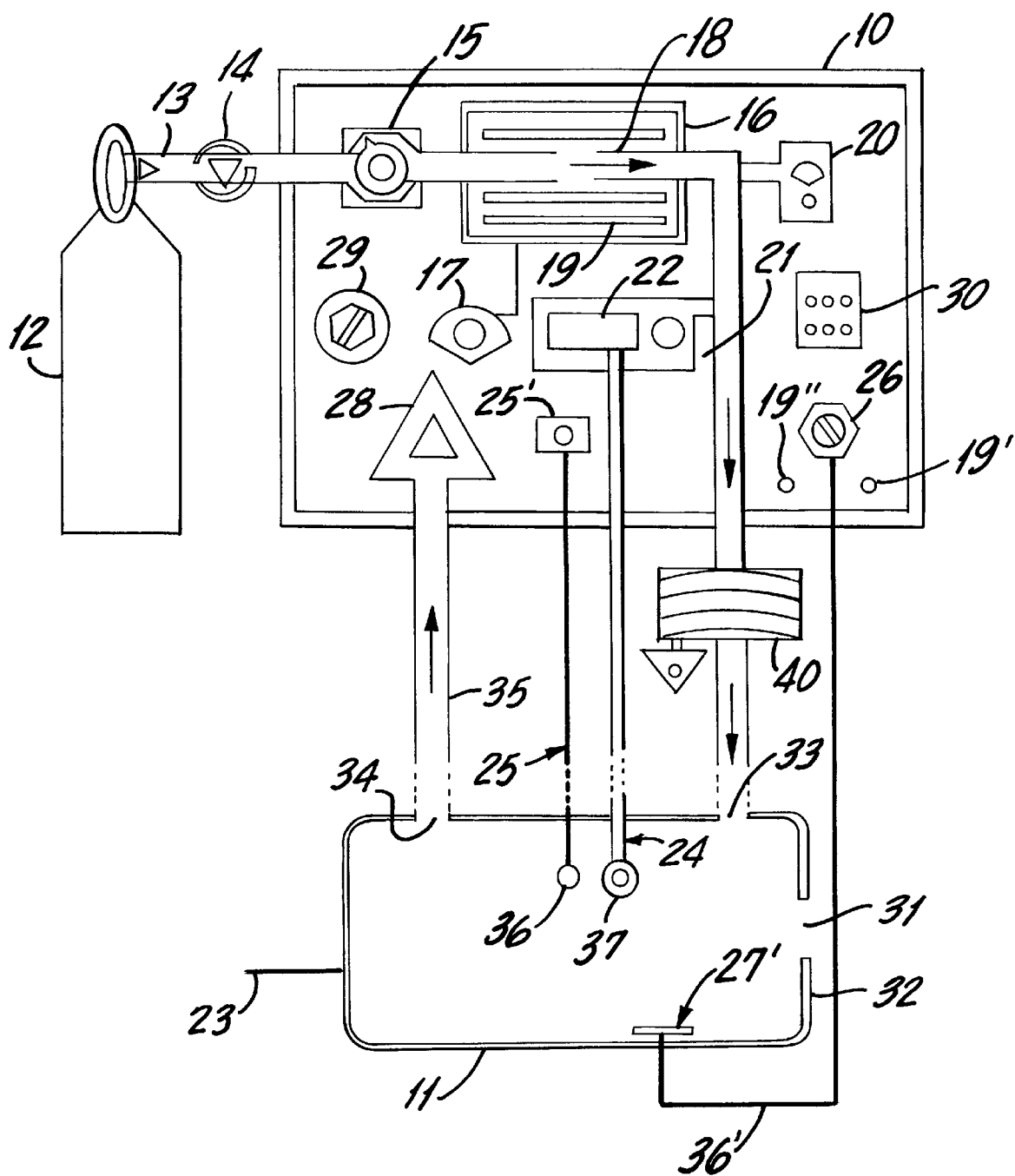

APPARATUS FOR THE APPLICATION OF OZONE/OXYGEN FOR THE TREATMENT OF EXTERNAL PATHOGENIC CONDITIONS

FIELD OF THE INVENTION

The present invention relates to a delivery system for providing ozone to treat an external pathogenic condition in an individual. It includes the drug manufacturing and delivery device as well as the technically advanced treatment envelope to surround the area having the pathogenic condition.

BACKGROUND OF THE INVENTION

Ozone has unique biological properties which are being investigated for applications in various medical fields.

As early as the First World War, ozone's bactericidal properties were used to treat infected wounds, mustard gas burns and fistulas. These first treatment attempts, however, were hampered by technological difficulties. Medical ozone generators have since been developed and refined. They differ from industrial generators in their capacity to deliver the purest ozone-oxygen mixtures in precise dosages A critical advance in medical ozone technology was the development, in the early 60's, of plastics which can adequately conduit this mixture and permit proper interfacing with patients. In the last few years ozone treatment has seen growing interest from diverse medical disciplines, and research is in progress to delineate its effects on biological systems and to define its clinical applications.

Historically, ozone was first administered by application to external body surfaces to determine its effects on a variety of lesions. Like natural rubber which cracks and fritters when exposed to oxygen-ozone mixtures, early materials to "bag" ozone around skin surfaces met with early oxidation disuse. Today, specially designed plastics (Teflon) enable extremities or portions of the head or torso to be comfortably encased in a space where a determined dosage ratio of oxygen to ozone is administered at a chosen flow rate. In this way, the walls of the transparent bags do not touch the patient, an important consideration in burn treatment.

Indications for external ozone application include poorly healing wounds, burns, staphylococcal infections, fungal and radiation lesions, herpes simplex and zoster, and gangrene (diabetic or Clostridium), among others. Dosage is adjusted to the condition treated. Gas perfusions may last from three to 20 minutes, ozone concentrations varying from 10 to 80 $\mu$g/ml (maximum five parts of ozone to 95 parts of oxygen). High ozone concentrations are used for disinfection and cleaning (or debridement), while low concentrations promote epithelialization and healing.

Payr in 1935 and Aubourg in 1936 first used ozone-oxygen mixtures in rectal insufflation to treat ulcerative colitis and fistulae. The list of indications have expanded to include proctitis and hemorrhoids. It is reported that in inflammatory diseases of the bowel, ozone promotes healing and restores the floral balance disturbed by pathogenic organisms. In a typical treatment for ulcerative colitis, daily insufflations are applied starting with 50 ml in severe cases, increasing as tolerated in increments (till 500 ml), high concentrations administered initially (75 $\mu$g/ml) to achieve hemostasis, followed by low concentrations to promote resolution. This technique may be of some promise in the treatment of bowel infections associated with AIDS. Microsporidia, a tiny, rarely detected parasite may be responsible for many cases of AIDS wasting illness, and studies await determination of its susceptibility to ozone treatment.

Most other medications are created by modifying the molecular structure of primary ingredients, through a series of biochemical steps, to arrive at the creation of biologically active molecules. The medication thus created will ultimately have a quantifiable measurement of its potency, usually translated into dosage (in milligrams or grams). It will also have some measure of biological availability over time. Thus, a medication could have a "shelf life" of several months or years.

Ozone, utilized as a medication, embodies a quantum conceptual development in drug administration and treatment. The mind set that has dominated our notion of what constitutes the identity of a drug must, in the case of ozone, be creatively modified. Ozone is a gas, and thus is not a solid palpable molecule. It does not have a shelf life. In fact, in one hour, at room temperature, approximately 50% of its content will have returned to pure oxygen. Ozone, in addition, cannot be stored except under extreme conditions of cold.

Ozone is a novel drug, and unlike other medications, needs to be manufactured at the time it is administered to the patient.

SUMMARY OF THE INVENTION

The present invention relates to an apparatus for the treatment of external pathogenic conditions in an individual. The apparatus, in general, comprises an ozone generation portion and a delivery portion. The delivery portion involves specially designed treatment envelopes and the ability to return ozone to the generator for reconversion to oxygen. The delivery portion also contains sensors to monitor dosage.

BRIEF DESCRIPTION OF THE FIGURE

The FIGURE shows a schematic of the ozone generator and the treatment envelope.

DETAILED DESCRIPTION OF THE INVENTION

The invention is a delivery system for providing ozone to a patient having an external pathogenic condition. The system comprises an ozone generation portion and a delivery portion. The generation portion comprises a source of oxygen connected to an ozone generator which provides an ozone-containing gas. There is at least one pressure controller to maintain gas pressure levels within a selected range within the apparatus. An ozone concentration analyzer is also included at least in the generator which measures ozone concentration in the ozone-containing gas. A humidifier for adjusting the humidity of the ozone-containing gas and a means for delivering the ozone-containing gas to the delivery portion is also included in the generator portion. The delivery portion comprises a flexible envelope for encompassing a portion of the patient which is to be treated. The envelope has an opening for inserting the patient portion to be treated and this opening is adapted to seal the inserted patient portion hermetically from an exterior of the envelope. The envelope has a probe for measuring the humidity of the ozone-containing gas and the envelope also a means for conducting the ozone-containing gas from the envelope to the generator portion.

The ozone-containing gas which is conducted from the envelope back to the generator portion is converted to oxygen in a conversion means in the generator portion. The ozone generator portion of the generator portion can be a coronal discharge ozone generator. The ozone generator further comprises a controller for controlling amperage flow within the coronal discharge ozone generator and also comprises a means for controlling the temperature of an environment within the coronal discharge ozone generator.

The flexible envelope is made of a material such that the patient portion being subjected to the ozone-containing gas may be seen from the exterior of the envelope. The flexible envelope further comprises a probe for determining a humidity level of the ozone-containing gas within the flexible envelope and a probe for measuring a temperature of the patient and a probe for measuring an ozone concentration of the ozone-containing gas within the flexible envelope.

The present invention comprises an ozone drug generation 10 and delivery system 11 which is symbiotically connected to the integrity and purity of the ozone drug itself. It is also designed to facilitate the setting of drug dosage factors at the time of treatment, in a dynamic and interactive relationship to the condition being treated.

Ozone is a gas whose properties are subject, among other factors, to temperature and time. In other words, a quality assured ozone generator has the capacity of producing ozone of high purity and of precise concentration. In the achievement of this task, however, the ozone generator needs to integrate several important features, namely the following:

1. The purity of the oxygen as the primary starting ingredient. Oxygen from which ozone is made needs to be of the highest quality (medical grade). The oxygen must be free of contaminant gases and, very importantly, must be devoid of nitrogen, due to the fact that the creation of nitrogen oxides may be biologically detrimental.
2. The flow rate of oxygen into the generator is an important determinant to the ozone concentration. At a given intensity of coronal discharge (amperage), a more rapid oxygen flow rate will result in lower ozone concentrations. The converse is equally applicable.

In ozone generators designed for external clinical applications, oxygen flow needs to be adjusted to the demands of the condition being treated. The present apparatus includes an oxygen supply 12 which is connected to a conduit 13 for the oxygen and generated ozone. The flow of $O_2$ through conduit 13 is controlled by $O_2$ flow valve 14 and $O_2$ flow meter 15.

For example, in the insufflation of an above-knee treatment envelope containing 50 liters, relatively rapid and efficient rate of filling of the envelope is desirable, so that the patient being treated may not have to spend an inordinate amount of time in the treatment procedure. In such a situation, a generator capable of producing biologically active ozone at the rate of 5 to 10 liters per minute would be ideal. Ozone ($O_3$) is generated from the $O_2$ in coronal discharge $O_3$ generator 16. The present apparatus further comprise:

3. An energy modulator. The power of the coronal discharge used to form 03 is directly related to the electrical energy provided to the oxygen flow. The stronger the amperage as measured by the coronal amperage gauge 17 channeled to the coronal discharge, the greater its potential for the generation of ozone. The modulator regulates the amperage, which directly correlates with ozone production requirements. The coronal amperage gauge 17 with fine tuning capacity is provided to enable the clinician and/or technician to modulate, in a precise fashion, the electrical flow provided to the ozone tubes.

The electrical current output to the ozone generating tubes 18 creates thermal energy. As the ozone generating tubes 18 become warmer, their efficiency diminishes, and ozone production begins to show concentration variabilities and inconsistencies.

The solution to this problem in the present apparatus is to provide water cooling 19 to the ozone tubes. This feature allows ozone production to follow much more reliable quantitative parameters over long periods of time, which far outlast ordinary treatment time protocols.

4. The system internal pressure. Starting with the oxygen flow and pressure into the generator, the pressure of the gas throughout the system is also important to ensure reliable ozone production. The internal pressure of the system may be said to possess a therapeutic range, whereby pressures below a certain level, as well as pressures above certain thresholds, will not be in harmony with other essential factors involved in ozone generation, and thus are apt to lead to unreliable ozone concentration readings.

The instant system is monitored by an internal system gas pressure gauge 20 which translates internal operating pressure into "Bar" readings—from 0 to 3 Bar (One Bar is equal to one atmospheric unit of pressure).

5. The ozone concentration provided by the generator. The ozone concentration analyzer 21 provides an accurate digital readout measured in micrograms per milliliter, or in grams per cubic meter.

The ozone concentration provided by the ozone concentration analyzer 21 directly measures ozone content by means of ultraviolet photometry. However, in order to accurately measure ozone concentration, the ozone concentration analyzer 21 needs to integrate atmospheric pressure and temperature. A digital readout 22 thus provides the clinician with a measurement of ozone generation, adjusted for temperature and barometric pressure.

Ozone concentrations appropriate to external medical applications usually range from 3% ozone/97% oxygen, to 6% ozone/94% oxygen.

6. The ozone concentration's measured in the treatment envelope 23. The ozone concentration analyzer 21 (which may be the same one used in #5, but is accessed through a switch), informs the clinician to the ozone concentration present in the envelope 23 via envelope ozone concentration probe 24. (See section on Treatment Envelope).
7. The humidity of the gas mixture in the treatment envelope is provided by gas humidity gauge 25. (see section on Treatment Envelope).
8. The dermal temperature of the patient surrounding the lesion under treatment is shown by patient temperature gauge 26 and sensor 27'. (See section on Treatment Envelope).
9. The ozone catalytic system 28 is important because it converts ozone exiting the treatment envelope 23 into oxygen. Ozone is thus prevented from escaping into the ambient environment.
10. The timer 29 of the generator 10 provides the clinician with: (1) The total time span of the treatment, which may be pre-programmed, and (2) The total dose of the ozone administered, factoring the functions of dosage and time.
11. The computer interface 30. The main generator 10 has the capacity to provide the following data to a computer system, thus enabling the clinician to follow the treatment parameters and the clinical progress of the patient.

c. The oxygen flow rate (from flow meter 15);
f. The internal system gas pressure (in Bars) from gauge 20;
h. The ozone concentration analyzer (in ug/ml), at the generator exit from analyzer 21;
S. The amperage delivered to the coronal discharge from gauge 17;
m. The ozone concentration in the envelope from probe 24
q. The envelope gas humidity from gauge 25;
i. The patient's skin temperature from sensor 27 and gauge 25;
t. Time functions; and
g. Memory functions.

THE TREATMENT ENVELOPE

The purpose of the treatment 11 envelope is to enclose the patient's external lesion so that it may be exposed to the ozone/oxygen mixture.

The envelope 11 is made from transparent polyethylene (or similar) material. Any material which is elastic and which is resistant to substantial degradation by ozone can be employed. Exemplary materials include polyolefin homo- and copolymers, polyesters, and Teflon. The transparency assures that the clinician will be able to fully observe the area under treatment at all times.

The envelope 11 needs to accurately fit the anatomy of the patient, so that the open end of the envelope 31 which accepts the insertion of a limb, or is affixed to an area on the patient's body, is firmly juxtaposed to the patient's skin. This is important inasmuch as an hermetic apposition will prevent treatment gases from escaping into the ambient air.

The rim of the envelope should therefore be made of a soft foamy strip 32 which will easily adopt the contours of the patient's anatomy, and will be constructed in such a way as to either:

1. Adhere directly to the skin by means of a contact strip, or
2. Be configured so as to enable it to be attached to the skin by means of surgical tape.

The envelope 11 has to have certain size parameters depending upon the area to be treated. Appropriate sizing of the envelope is very important to the proper delivery of treatment gases, to their adequate flow around the lesions, and to the accurate measurement of their concentrations.

The envelope 11, when inflated, must clear the entire treatment area, and not touch any skin surface. This is important in the therapy of burns, for example, since any contact with the delicate granulation layer may injure it, and thus delay healing.

In the calculation of the optimal gaseous volume which must serve a given area of skin surface, the following formula is offered:

For every 100 $cm^2$ of skin, at least 2 liters of gaseous space is needed in order to provide adequate gas distribution and biological interaction. For example, in the case of a decubitus ulcer in the sacral region, measuring 5 centimeters in diameter, for example, an area of at least 10×10 centimeters would be designated as the treatment area. A treatment envelope 11 whose base opening 31 would accommodate these dimensions would be applied around the ulcer, and its minimal volume would be 2 liters.

A similar process would be applied to the encasement of an afflicted hand or leg. In an above-knee situation where the envelope is affixed to the upper leg, the potential volume of the enclosed treatment space may reach 50 to 75 liters.

It is apparent that many sizes and shapes of envelopes would need to be designed to accommodate anatomical regions. In addition, depending upon the clinical situation encountered (i.e. herpes of the face), custom created envelopes would have to be designed.

On one side of the envelope is an ozone inlet 33 which may be equipped with an appropriate unidirectional valve which prevents the return of the ozone/oxygen mixture into the generating unit 10. This inlet U receives the ozone/oxygen mixture delivered by the generator 10.

Situated some distance away from the inlet opening is the outlet port 34, which may also be equipped with a unidirectional valve which prevents the return of the oxygen/ozone mixture back into the envelope 11. A tube 35 exits from this port and is directed to the ozone catalyzer 28. The catalyzer 28 converts ozone exiting from the treatment envelope 11 into oxygen.

Embedded into the surface area of the envelope 11 are 2 portholes 36, 37. These allow for the hermetic insertion of probes 25, 24 which provide readings of envelope contents during treatment. These probes 25, 24 enter the envelope 11 itself, and are connected to the generator unit 10.

The following values are measured by these probes 25, 24, namely:

1. The ozone concentration within the envelope, probe m. Indeed, although the generator 10 is able to provide a readout of the ozone concentration at its exit, the ozone concentration inside the envelope may be different for a variety of reasons.

Amongst these is the fact that the envelope 11, when initially affixed to the patient contains some amount of air which needs to be displaced by ozone, especially during the initial phase of the treatment. During the time of insufflation, the envelope ozone reading will gradually rise as the ozone/oxygen mixture reaches its desired level. The envelope ozone concentration may also vary because of the relatively short half life of ozone, uneven gaseous circulation within the envelope and, in addition, by the absorption of ozone by diseased tissues.

This probe 24 is connected to the ozone analyzer 21 located in the main unit 10. The ozone analyzer 21 is a device which primarily functions by means of an ultraviolet photometer.

The clinician is therefore provided with a more accurate measurement of the actual dosage of ozone applied to the patient's skin at any one time. A toggle switch (not shown) will give the clinician the option to be appraised of the generator output on one hand, and of the actual envelope ozone concentration on the other. Both of these values will be offered in a digital display mode(22).

2. The humidity content present in the envelope 11 at the time of the treatment. Ozone/oxygen administered in dry form has different properties than that given in the presence of water vapor. Certain clinical conditions respond more appropriately to dry gas administration (i.e. the rim of a decubitus ulcer), while others, especially those involving infectious organisms, are much more prone to be inactivated when the administered gas is humid.

Interfacing the generator and the treatment envelope will be a humidifier L (FIG. 1). A gas line running in parallel will enable different proportions of the 02/03 mixture to be humidified. The humidity probe 25 inserted into the envelope 11 will be connected to the main unit 10, and will inform the clinician of the gaseous mixture's humidity concentration as it is delivered to the lesion. Accordingly, this humidity level may be adjusted to fit clinical needs.

THE TEMPERATURE PROBE

The temperature probe 26 is mentioned in this section because it is an instrument that guides the clinician to provide an even greater participation in the treatment procedure.

Ozone works in its healing capacity through two main avenues, one of which is its pan-antipathogenic properties. The other is its stimulating effects, at proper concentrations, upon the vascular and lymphatic circulations. The exact mechanisms underlying this phenomena continue to need clarification. It is possible that ozone assists in the creation of vascular nitric oxide, a gas which has stimulated major interest for its role in arterial and arteriolar dilatation, thus promoting a beneficial lowering of blood pressure.

Increased and more efficient circulation provides for 1) greater oxygenation to tissues; 2) improved immunological availability to the pathological process; 3) the enhanced generation of healthy tissues and 4) the more efficient removal of waste material. Documented effects of ozone on blood dynamics include ameliorated fluidity through improved erythrocyte pliability. In addition, ozone directly stimulate glycolysis.

At times, the clinician will be interested in the skin temperature as a measure of ozone's vasostimulating capacity. In order to enhance circulation, ozone concentration in the envelope may need to be increased; in other cases, paradoxically, ozone concentrations which are too high, may lead to vasoconstriction, and the envelope ozone concentration may then have to be lowered.

In any event, the clinician is provided with a digital readout of the patient's skin temperature proximal to the lesion receiving treatment, and may thus make appropriate adjustments.

The temperature probe 26 is essentially a wire which incorporates a sensor specially geared to the ranges of temperature generated by the mammalian skin. The probe 27 is taped to the patient's skin, at a distance from the lesion the clinician deems appropriate.

The wire 36 is led through the bottom of the envelope 11 (FIG. 2), and is connected to the main generating unit where it yields a digital readout of the patient's skin temperature.

INTEGRATING TOPICAL OZONE THERAPY WITH MICROBIOLOGY

The therapy of infected wounds, poorly healing lesions, decubitus ulcers, and diabetic ulcers, among many conditions in which many infective organisms contribute to their pathogenesis, is invariably complicated by the determination of the most important pathogen(s) involved in the disease process. Once identified, a best choice of antibiotic, topical and/or systemic, is normally selected from appropriate sensitivity studies. In this common scenario, usually one or two pathogens will be singled out for inactivation, while the pathogenic role of many others will not be able to be addressed.

In actual situations, the infected lesions mentioned above are usually invaded by a pan-pathogenic spectrum of organisms, any one of which may exert its own significant nefarious influence. In other words, the identification of one or even two putative organisms and their corresponding inactivation, may provide for only a partial, or even minimal, therapeutic intervention.

Thus the reason for the term "poorly healing wounds". Among the many reasons for the refractoriness of these wounds to antipathogen therapy is the multiplicity of infective agents present, both aerobic and anaerobic.

The ideal pan-pathogenicidal agent needs to be capable of inactivating a spectrum of offending microbes, whether bacterial, viral, fungal, or parasitic.

Ozone, properly utilized is, in fact, such an agent.

The partial list of organisms susceptible to ozone inactivation include the following:

1. Aerobic and Anaerobic bacteria: Bacteroids, Campylobacter, Clostridium, Corynebacteria, Escherichia, Klebsiella, Legionella, Mycobacteria, Proprionobacteria, Pseudomonas, Salmonella, Shigella, Staphylococcus, Streptococcus, Yersinia.
2. Viruses: Adenoviridae, Filiviridae, Hepnaviridae (Hepatitis B and C), Herpesviridae (Herpes I and II, Cytomegalovirus, Epstein-Barr), Orthomyxoviridae (Influenze A and B), Picomaviridae (Poliovirus, Coxsachie, Echovirus, Rhinovirus, Hepatitis A and E), Reoviridae (Rotavirus), and Retroviridae (HIV-I, WHV-II).
3. Fungi: Actinomycoses, Aspergillus, Candida, Cryptococcus, Epidermophyton, Histoplasma, Microsporum, Trichophyton. Susceptible dermatophyte infections include Tinea Pedis, tinea Unguium, Tinea cruris, and Tinea Capitis.
4. Protozoa: Amoeba species, Giardia lamblia.

In the field of microbiology, infective agents need first to be identified. Secondly, through laboratory procedures involving testing the sensitivity of the organism to a variety of antimicrobials, a "best antibiotic" is normally identified, and the therapy of the patient's lesions begins.

Proposed herewith, is a similar process for ozone. In the hypothetical case of the patient with the cited poorly healing lesions, cultures of the lesions are taken. Both aerobic and anaerobic bacteria growth media are utilized in order to provide investigative coverage to a comprehensive spectrum of possible families of putative microorganisms.

The organisms, once cultured, are then exposed to varying concentrations of ozone, in specially constructed laboratory hoods. Suggested gradients of ozone concentrations may be 1% ozone with 99% oxygen, 2%, 3%, 4%, and 5% ozone. The laboratory data will reveal the optimal ozone concentration that will efficiently inactivate the greatest percentage of pathogens.

In individual conditions to be treated, it is assumed that the greater the ozone concentration and the more prolonged the duration of exposure, the greater its killing power. While this is generally the case, it must be remembered that it is not solely the lesion that is being treated, but the entire patient. In an important number of clinical scenarios (i.e. in infected deep bums, or in severe radiodermatitis), lesser, rather than greater ozone concentrations may need to be applied for special treatment considerations.

It is in these cases that laboratory corroboration of ozone concentration versus optimal pathogen killing power would be clinically relevant. Thus, as a drug in its own right, ozone would benefit from the same scientific validation and laboratory confirmation as all other anti-infective agents.

Although the foregoing invention has been described in some detail by way of illustration and example for purposes of clarity of understanding, it will be obvious to those skilled in the art that certain changes and modifications may be practiced without departing from the spirit and scope thereof as described in the specification and as defined in the appended claims.

What is claimed is:

1. A delivery system for providing ozone to an external portion of a patient having a pathogenic condition, the system comprising an ozone generation portion and a delivery portion, said ozone generation portion comprising a source of medical grade oxygen connected to an ozone generator which provides an ozone containing gas, at least one pressure controller to maintain gas pressure levels within a selected range, an ozone concentration analyzer which measures ozone concentration in the ozone containing gas and a humidifier for adjusting the humidity of the ozone containing gas and a means for delivering said ozone containing gas to the delivery portion at an ozone concentration in the range of 1% O3/99% O2 to 6% O3/94% O2, the delivery portion comprising a substantially completely flexible envelope for encompassing a portion of a patient; said envelope having an opening for inserting a portion of such patient and said opening including means for sealing such an inserted portion of such patient from the exterior environment; said flexible envelope having probes for measuring humidity and the O3 concentration of the ozone containing gas and the dermal temperature of such a portion of such a patient within the substantially completely flexible envelope; and means for conducting the ozone containing gas from said substantially completely flexible envelope to said ozone generator portion.

2. The delivery system of claim 1, wherein the ozone-containing gas conducted from the substantially completely flexible envelope to the ozone generator portion is converted to medical grade oxygen in a conversion means in said ozone generator portion.

3. The delivery system of claim 1, wherein the ozone generator is a coronal discharge ozone generator.

4. The delivery system of claim 3, wherein the coronal discharge ozone generator comprises a controller for controlling amperage flow within said coronal discharge ozone generator.

5. The delivery system of claim 4, wherein the coronal discharge ozone generator further comprises means for controlling the temperature of an environment within said coronal discharge ozone generator.

6. The delivery system of claim 1, wherein the substantially completely flexible envelope is made of a material such that a patient portion being subjected to the ozone-containing may be seen from the exterior of said substantially completely flexible envelope.

7. The delivery system of claim 6, wherein the substantially completely flexible envelope further comprises a probe for determining the humidity level of the ozone-containing gas within said substantially completely flexible envelope.

8. The delivery system of claim 6, wherein the substantially completely flexible envelope further comprises a probe for measuring the temperature of a patient.

9. The delivery system of claim 6, wherein the substantially completely flexible envelope further comprises a probe for measuring the ozone concentration of the ozone-containing gas within said substantially completely flexible envelope.

* * * * *